US011166692B2

United States Patent
Okutani et al.

(10) Patent No.: US 11,166,692 B2
(45) Date of Patent: Nov. 9, 2021

(54) X-RAY IMAGE DIAGNOSTIC APPARATUS

(71) Applicant: SHIMADZU CORPORATION, Kyoto (JP)

(72) Inventors: Keita Okutani, Kyoto (JP); Masahiro Tanaka, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 16/689,576

(22) Filed: Nov. 20, 2019

(65) Prior Publication Data
US 2020/0085399 A1 Mar. 19, 2020

Related U.S. Application Data

(63) Continuation-in-part of application No. 16/259,607, filed on Jan. 28, 2019, now abandoned.

(30) Foreign Application Priority Data

Mar. 30, 2018 (JP) .............................. JP2018-66679
Mar. 29, 2019 (JP) ............................. JP2019-066531

(51) Int. Cl.
A61B 6/00 (2006.01)
A61B 6/04 (2006.01)

(52) U.S. Cl.
CPC .............. A61B 6/54 (2013.01); A61B 6/0407 (2013.01); A61B 6/0487 (2020.08);
(Continued)

(58) Field of Classification Search
CPC ..... A61B 6/0407; A61B 6/102; A61B 6/4447; A61B 6/461; A61B 6/481; A61B 6/487;
(Continued)

(56) References Cited

U.S. PATENT DOCUMENTS

2004/0228439 A1* 11/2004 Tsujii ....................... A61B 6/06
378/62
2005/0195945 A1* 9/2005 Gotoh .................. A61B 6/4014
378/197

(Continued)

FOREIGN PATENT DOCUMENTS

JP 2001-000428 A 1/2001

OTHER PUBLICATIONS

U.S. Appl. No. 16/689,576, Office Action dated Apr. 9, 2020, 9 pages.

Primary Examiner — Chih-Cheng Kao
(74) Attorney, Agent, or Firm — Andrew F. Young; Nolte Lackenbach Siegel

(57) ABSTRACT

An X-ray image diagnostic apparatus images a subject with X-rays without increasing the burden on a user, and includes an X-ray image diagnostic apparatus 1, a table 4 on which a subject is placed on the top-surface thereof; an X-ray tube 5 disposed beneath the back side of the table and which emits X-rays; a detector 6 disposed above the table 4 so as to face the X-ray tube 5 and detecting the X-rays emitted from the X-ray tube 5 and penetrating the subject on the table 4; an X-ray tube moving mechanism 12 that moves the X-ray tube 5 in a direction approaching the table 4 and moving away therefrom; a detector moving mechanism 13 that moves the detector 6 in a direction approaching the table 4 and moving away therefrom; and a control unit 14 that controls a distance between the X-ray tube 5 and the detector 6 by controlling action of the X-ray tube moving mechanism 12 and the detector moving mechanism 13.

10 Claims, 12 Drawing Sheets

(52) U.S. Cl.
CPC .......... *A61B 6/4291* (2013.01); *A61B 6/4476* (2013.01); *A61B 6/588* (2013.01); *A61B 6/589* (2013.01); *A61B 6/587* (2013.01); *G06T 2207/10116* (2013.01)

(58) Field of Classification Search
CPC ..... A61B 6/547; A61B 6/0457; A61B 6/4291; A61B 6/54; A61B 6/588; A61B 6/0487; A61B 6/589; A61B 6/4476
See application file for complete search history.

(56) References Cited

U.S. PATENT DOCUMENTS

| | | | | |
|---|---|---|---|---|
| 2009/0272907 | A1* | 11/2009 | Hara | A61B 6/0487 250/370.09 |
| 2016/0166230 | A1* | 6/2016 | Kim | A61B 6/06 378/205 |
| 2018/0235559 | A1* | 8/2018 | McCarthy | A61B 6/589 |

* cited by examiner

X-RAY IMAGE DIAGNOSTIC APPARATUS

CROSS REFERENCE TO RELATED APPLICATIONS

This application relates to, and claims priority from SN JP 2019-066531 filed Mar. 29, 2019, the entire contents of which are incorporated herein by reference.

This application additionally relates to, and claims priority as a continuation-in-part (CIP) from U.S. Ser. No. 16/259,607 filed Jan. 28, 2019 which relates to, and claims priority from JP 2018-066679 filed Mar. 30, 2018, the entire contents of each of which are incorporated herein by reference.

FIGURE SELECTED FOR PUBLICATION

FIG. 1.

BACKGROUND OF THE INVENTION

Field of the Invention

The present invention relates to an X-ray image diagnostic apparatus.

Description of the Related Art

A variety of X-ray image diagnostic apparatuses includes an apparatus called a proximity fluoroscopic apparatus that is used when a user, such as medical doctor, takes an X-ray image of a subject, such as a patient, while the user operates the apparatuses in the proximity of the subject. With respect to such apparatuses, a proximity fluoroscopic apparatus; including an X-ray tube, which is provided beneath (below) a table on which the patient is placed, and a detector, which is provided above the table and detects X-rays emitted from the X-ray tube; is called an under-table (X-ray) tube proximity operation fluoroscopic imaging apparatus (for example, refer to Patent Document 1).

With respect to the conventional under-table tube proximity operation fluoroscopic imaging apparatus, whereas the detector is movable in a direction approaching or moving away from the table, the X-ray tube is not movable in a direction approaching or moving away from the table.

In addition, a scattered ray removal grid is mounted on the detector in order to suppress the influence of scattered rays.

As to the proximity fluoroscopic apparatus, a distance (source image distance: SID) between the X-ray tube and the detector is short, so that a convergence grid is used in many cases. With regard to the convergence grid, a transmission portion and an absorption portion are arranged depending on the convergence distance so as to be inclined at a predetermined angle in the thickness direction of the grid.

Therefore, when the SID becomes mismatched to the convergence distance of the grid, some of the X-rays emitted from the X-ray tube are absorbed by the absorption portion of the grid, so that a uniform image cannot be obtained. Accordingly, it is important to select a grid having an appropriate convergence distance matching to the SID.

For example, with respect to an under-table tube proximity fluoroscopic apparatus, the detector may be moved in a direction approaching or away from the subject (i.e., the table) depending on an imaging part (position of a region of interest) and/or the thickness (body thickness) of the subject. However, as described above, with respect to the conventional under-table tube proximity operation fluoroscopic imaging apparatus, the X-ray tube is immovable in a direction approaching or away from the table. Therefore, when the detector is moved in a direction approaching the table or moving away from the table, the SID dynamically changes resulting in mismatching to the convergence distance of the grid.

In the above case, the grid must be replaced by another grid having the convergence distance suitable for the SID, each time the SID changes, but such a task can be burdensome for the user.

RELATED PRIOR ART DOCUMENTS

Patent Document

Patent Document 1: JP Patent Published 2001-428 A1

ASPECTS AND SUMMARY OF THE INVENTION

Objects to be Solved

An object of the present invention is to provide an X-ray image diagnostic apparatus capable of imaging a subject with X-rays in accordance with a purpose without increasing the burden on a user.

Means for Solving the Problem

For the purpose to achieve the object, the X-ray image diagnostic apparatus according to the first aspect of the present invention comprises: a table that has a top-surface (front-surface) and a back-surface, wherein a subject is placed on the top-surface thereof; an X-ray source that is disposed on the beneath side of the table and emits X-rays to the subject; a detector that is disposed on the top-surface (above) side of the table so as to face the X-ray source and detects the X-rays that are emitted from the X-ray source and penetrating the subject placed on the table; a first moving mechanism that moves the X-ray source in a direction approaching the table or moving away therefrom; a second moving mechanism that moves the detector in a direction approaching the table or moving away therefrom; and a control unit that controls a distance between the X-ray source and the detector by controlling actions of the first moving mechanism and the second moving mechanism.

With respect to the X-ray image diagnostic apparatus according to the first aspect of the present invention, as described above, the control unit individually controls the movement of the X-ray source by the first moving mechanism and the movement of the detector by the second moving mechanism. Therefore, the operability of the X-ray image diagnostic apparatus is high, so that the positional relationship between the X-ray source and the detector can be set with more freedom.

With respect to the X-ray image diagnostic apparatus according to the first aspect of the present invention, it is preferable that the control unit controls the action of the second moving mechanism in response to an input from an operator and also, the action of the first moving mechanism so as to move the X-ray source is moved interlockingly with movement of the detector according to the control using controlled by the second moving mechanism. According to such a configuration described above, for example, the X-ray imaging of the subject can be more easily performed in accordance with the purpose without increasing the burden on the user.

With respect to the X-ray image diagnostic apparatus in which the X-ray source is moved interlockingly with the movement of the above detector, it is preferable that the control unit controls the action of the first moving mechanism in order to keep a distance (SID) between the X-ray source and the detector so as to be constant in a movable range of the X-ray source. According to such a configuration described above, the X-ray imaging of the subject can be performed in the optimal state for the purpose of keeping the SID to be constant. being constant.

In such a case, it is preferable that the X-ray image diagnostic apparatus further comprise: a mounting unit that enables mounting a grid for removing a scattered ray on the detector; and a grid detection unit that detects the kind of the grid and determines whether such a grid is mounted onto the mounting unit or not, wherein the control unit determines the away distance in accordance with the kind of the grid detected by the grid detection unit. According to the configuration described above, the convergence distance of the grid and the SID always match with each other. Therefore, most of the X-rays emitted from the X-ray source transmit a transmission portion of the grid, so that a uniform (homogeneous) X-ray image of the subject can be obtained. As a result, the accurate diagnosis can be achieved based on the obtained image.

With respect to the X-ray image diagnostic apparatus in which the X-ray source is moved interlockingly with the movement of the above detector, it is preferable that the control unit controls the action of the first moving mechanism so that an enlargement ratio of an X-ray image of the subject is kept being constant. According to such a configuration described above, the X-ray imaging of the subject can be performed in the optimal state for the purpose of keeping the enlargement ratio, which should be constant, of the image.

With respect to the X-ray image diagnostic apparatus according to the above aspect of the present invention, it is preferable that the X-ray image diagnostic apparatus further comprises a lifting mechanism that moves up and down the table in a horizontal state together with the first moving mechanism and the second moving mechanism, and the control unit can control the action of the first moving mechanism in order to move the X-ray source interlockingly with moving up and down the table in the horizontal state by the lifting mechanism. According to such a configuration described above, for example, the table can be brought much closer to the installation surface on which the X-ray image diagnostic apparatus is installed. As a result, such a configuration facilitates the subject to get on and off of the table.

In such a case, it is preferable that the control unit controls the action of the first moving mechanism in order to move the X-ray source in a direction approaching the table when an away distance between an installation surface on which the X-ray image diagnostic apparatus is installed and the X-ray source provides a predetermined value. According to such a configuration described above, the X-ray source can be prevented from colliding with the installation surface, which causes a damage, and the table can be set closer to the installation surface (i.e., the table can be lowered much closer to the lower position).

For the purpose to achieve the object, the X-ray image diagnostic apparatus according to a second aspect of the present invention comprises: a table that has a top-surface and a back-surface, wherein a subject is placed on the top-surface thereof; an X-ray source that is disposed on the beneath side of the table and emits X-rays to the said subject; a detector that is disposed above the top-surface side of the table so as to face the X-ray source and detects the said X-rays that are emitted from the X-ray source and transmitting the subject placed on the table; a moving mechanism that moves the X-ray source in a direction approaching the table and moving away therefrom; a lifting mechanism that lifts the table together with the moving mechanism while the table is horizontal; a control unit that controls lifting the X-ray source in association with lowering the table by controlling actions of the moving mechanism and the lifting mechanism.

With respect to the X-ray image diagnostic apparatus according to the second aspect of the present invention, as described above, the control unit is capable of lifting the X-ray source in association with lowering the table. Accordingly, the X-ray source can be prevented from colliding with the installation surface on which the X-ray image diagnostic apparatus is installed, which causes a damage, and the table can be set closer to the installation surface (i.e., the table can be lowered much closer to the lower position). And the subject can easily get on and off from the table, so that the X-ray imaging of the subject can be easily performed in accordance with the purpose.

With respect to the X-ray image diagnostic apparatus according to the second aspect of the present invention, as described above, it is preferable that the control unit controls the action of the moving mechanism so as to lift the X-ray source when the away distance between the installation surface, on which said the X-ray image diagnostic apparatus is installed, and the X-ray source provides a predetermined value. According to such a configuration, the X-ray source can be prevented from colliding with the installation surface, which causes a damage, and the table can be set closer safely to the installation surface.

In such a case, it is preferable that the control unit lowers the table and the X-ray source until the away distance provides the predetermined value by controlling the action of the lifting mechanism, suspends lowering the table and the X-ray source when the away distance provides the predetermined value, and then lifts the X-ray source by controlling the action of the moving mechanism following suspending once. According to such a configuration, for example, the user enables to make sure the action from lowering to suspending the X-ray source and the action from suspending to lifting the X-ray source, action by action, so that the burden on the user can be reduced while using the X-ray image diagnostic apparatus.

Effects of the Present Invention

According to the present invention described above, for example, the X-ray imaging of the subject can be performed in accordance with the purpose without increasing the burden on the user.

According to another aspect of the present invention, there is provided an X-ray image diagnostic apparatus, comprising: a table that has a top-surface and a back-surface, wherein a subject is placed on the top-surface during a use of the X-ray image diagnostic apparatus, an X-ray source beneath the back-surface side of the table and which emits X-rays to the subject, a detector that is disposed above the top-surface side of the table to face the X-ray source and detect the X-rays emitted from the X-ray source and transmitting the subject placed on the table, a first moving mechanism that moves the X-ray source in a direction approaching the table and a direction moving away from the table, a second moving mechanism that moves the detector in a direction approaching the table and a direction moving away from the table, and a control unit that controls a distance between the X-ray source and the detector by controlling actions of the first moving mechanism and the second moving mechanism.

According to another aspect of the present invention, there is provided a X-ray image diagnostic apparatus, wherein: the control unit controls the action of the second moving mechanism in response to an input from an operator and further controls the action of the first moving mechanism that moves the X-ray source interlockingly with movement of the detector controlled thereby.

According to another aspect of the present invention, there is provided a X-ray image diagnostic apparatus, wherein: the control unit controls the action of the first moving mechanism that keeps a distance (SID i.e., source image distance) between the X-ray source and the detector being constant within a movable range of the X-ray source.

According to another aspect of the present invention, there is provided a X-ray image diagnostic apparatus, further comprising: a mounting unit that mounts a scattered ray removal grid on the detector, a grid detection unit that detects a mounting of the grid on the mounting unit and a kind of the grid, and wherein the control unit determines the distance based on the kind of the grid detected by the grid detection unit.

According to another aspect of the present invention, there is provided a X-ray image diagnostic apparatus, wherein: the control unit controls the action of the first moving mechanism so that an enlargement ratio of an image of the subject, obtained by using the X-rays, is being constant.

According to another aspect of the present invention, there is provided a X-ray image diagnostic apparatus, further comprising: a lifting mechanism that moves up-and-down the first moving mechanism together with the second moving mechanism when the table is horizontal, and wherein the control unit controls the action of the first moving mechanism so that the X-ray source moves interlockingly with the table that moves up-and-down using the lifting mechanism when the table is horizontal.

According to another aspect of the present invention, there is provided a X-ray image diagnostic apparatus, wherein: the control unit controls the action of the first moving mechanism so that the X-ray source moves in an approaching direction to the table when a distance between the installation surface on which the X-ray image diagnostic apparatus is placed and the X-ray source is a predetermined value.

According to another aspect of the present invention, there is provided a X-ray image diagnostic apparatus, comprising: a table that has a top-surface and a back-surface, wherein during a use a subject is placed on the top-surface of the table, an X-ray source that is disposed below the back-surface side of the table and emits X-rays to the subject, a detector that is disposed above the top-surface side of the table to face the X-ray source and which detects the X-rays emitted from the X-ray source and transmitting the subject placed on the table, a moving mechanism that moves the X-ray source in a direction approaching the table and moving away therefrom, a lifting mechanism that lifts the table together with the moving mechanism when the table is horizontal, and a control unit that controls lifting the X-ray source in association with lowering the table by controlling actions of the moving mechanism and the lifting mechanism.

According to another aspect of the present invention, there is provided a X-ray image diagnostic apparatus, wherein: the control unit controls the action of the moving mechanism so that the X-ray source lifts when a distance between an installation surface and the X-ray source provides a predetermined value, and the X-ray image diagnostic apparatus is installed on the installation surface.

According to another aspect of the present invention, there is provided a X-ray image diagnostic apparatus, wherein: the control unit lowers the table and the X-ray source until the distance provides the predetermined value by controlling an action of the lifting mechanism, suspends once lowering the table and the X-ray source when the distance provides the predetermined value, and then lifts the X-ray source by controlling the action of the moving mechanism.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
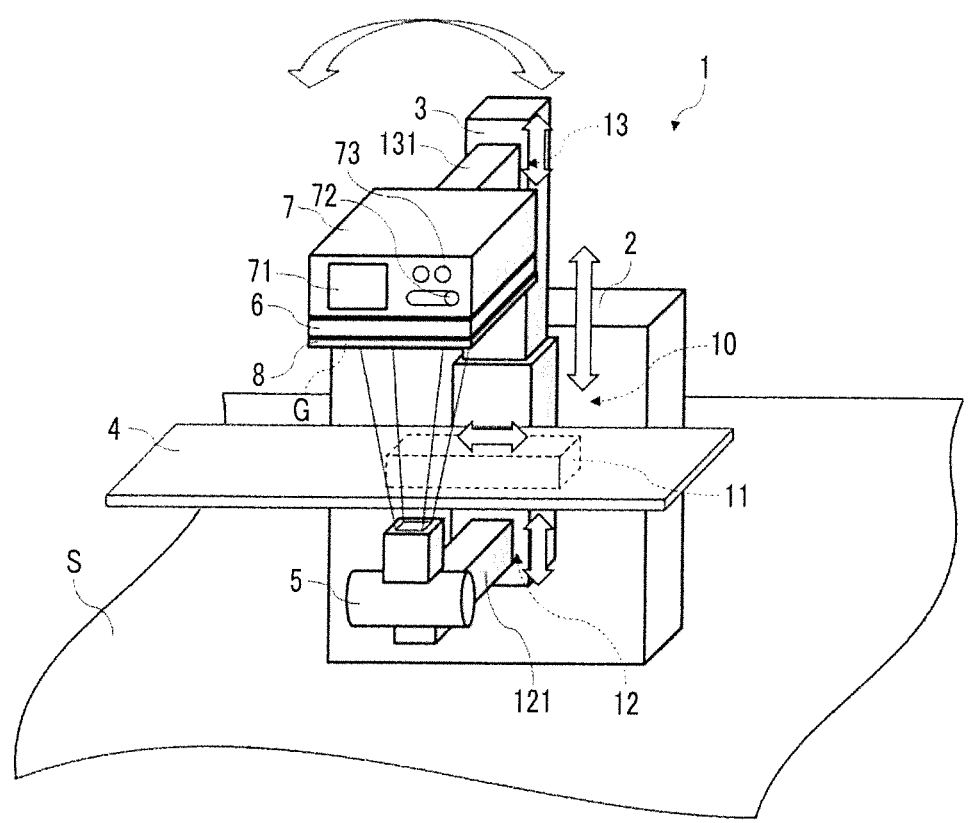
FIG. 1 is a schematic diagram illustrating the overall configuration of an X-ray image diagnostic apparatus according to an embodiment of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' or 'connect' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention, however, the order of description should not be construed to imply that these operations are order dependent.

Hereinafter, the inventors set forth an X-ray image diagnostic apparatus of the present invention in detail according to a preferred embodiment based on the accompanying diagrams.

Figure 2:
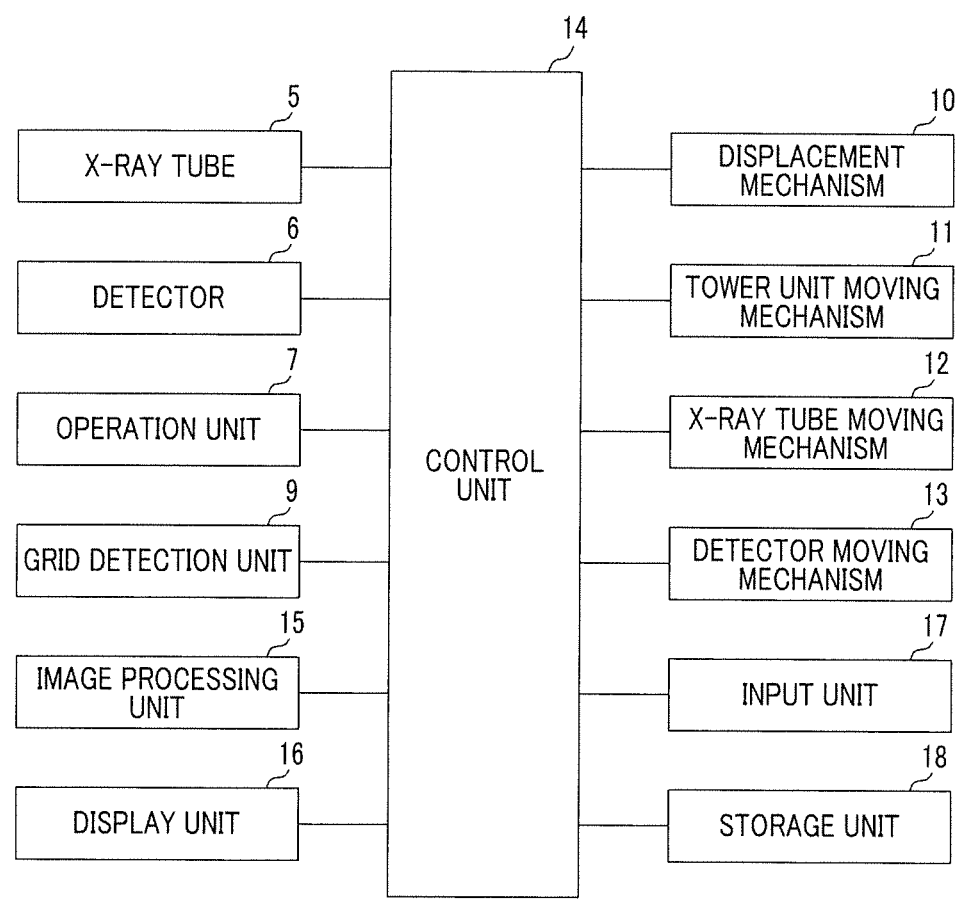
FIG. 2 is a block diagram of the X-ray image diagnostic apparatus shown in FIG. 1.
Figure 3:
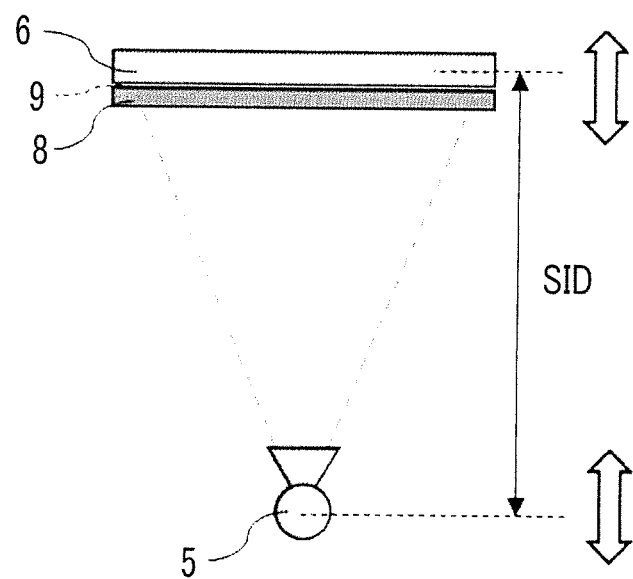
FIG. 3 is a diagram illustrating the positional relationship between an X-ray tube and a detector.
Figure 4A:
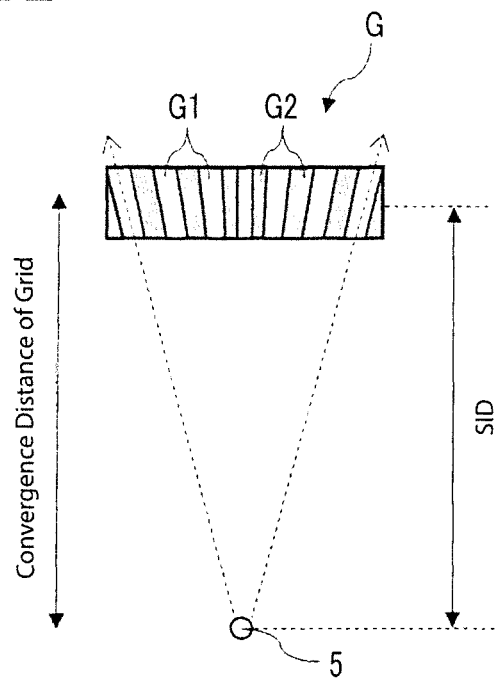
FIGS. 4A and 4B are diagrams illustrating the relationship between a grid and a SID.
Figure 4B:
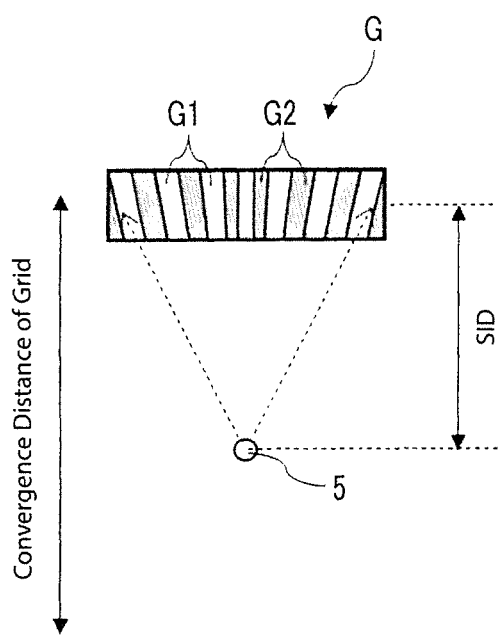
Figure 5A:
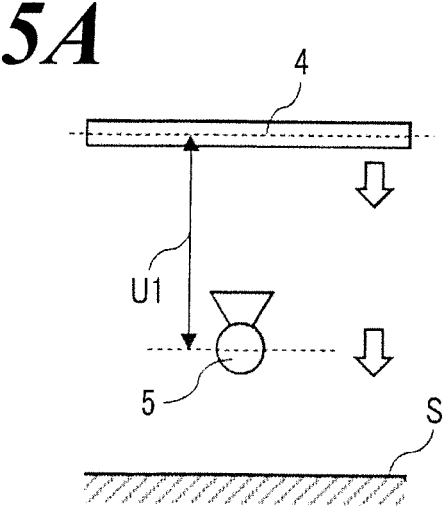
FIGS. 5A, 5B and 5C are diagrams illustrating the positional relationship between an X-ray tube and a table (the first action).
Figure 5B:
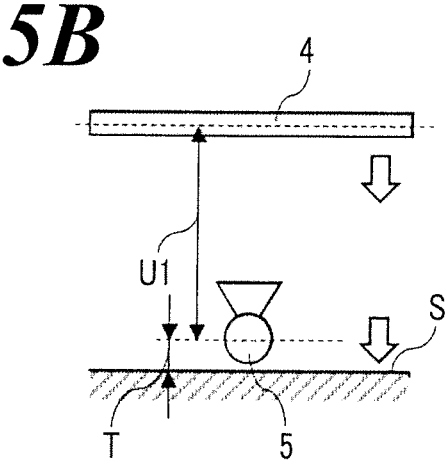
Figure 5C:
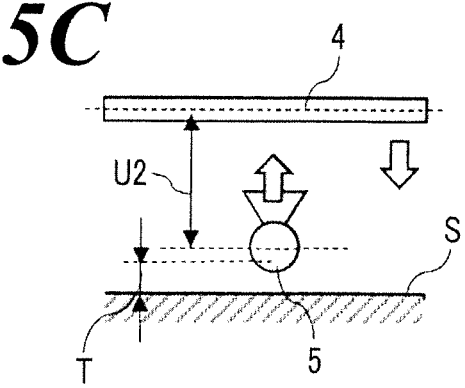
Figure 6A:
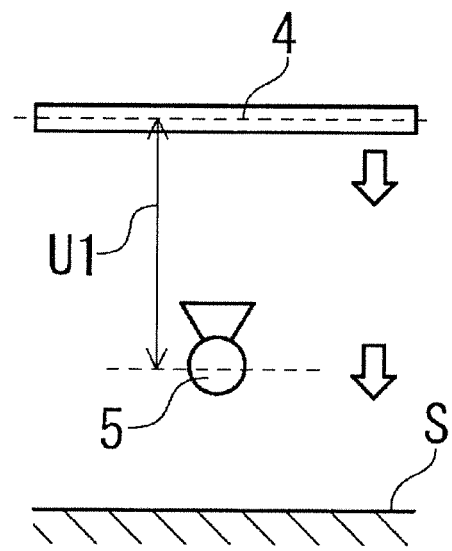
FIG. 6A, 6B, 6C, 6D, 6E are diagrams illustrating the positional relationship between an X-ray tube and a table (diagram of the second action).
Figure 6B:
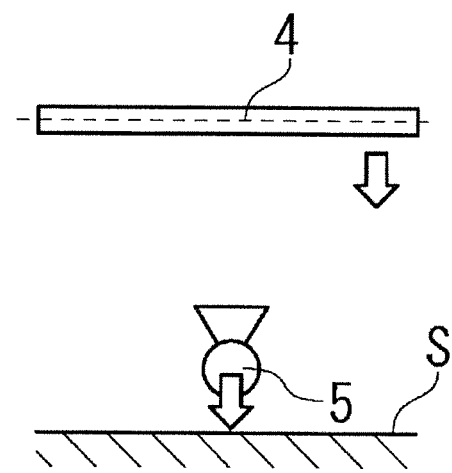
Figure 6C:
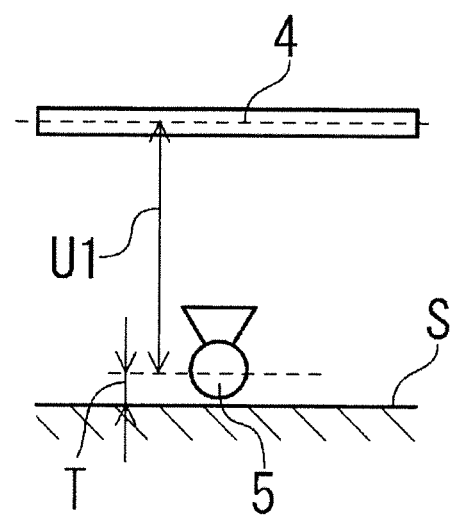
Figure 6D:
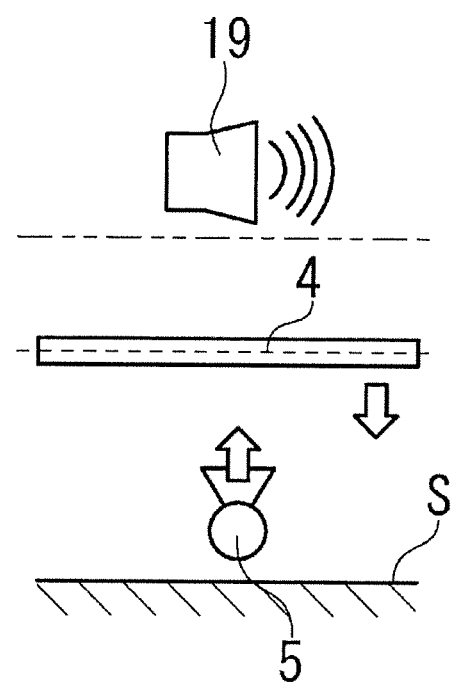
Figure 6E:
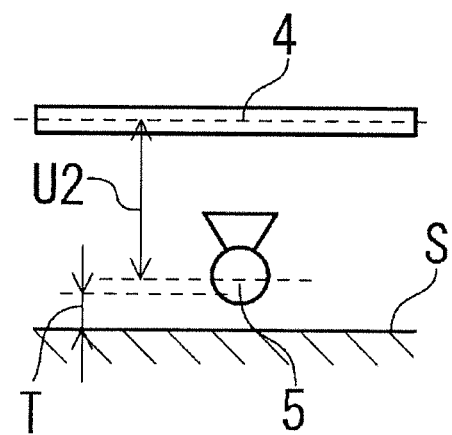
Figure 7:
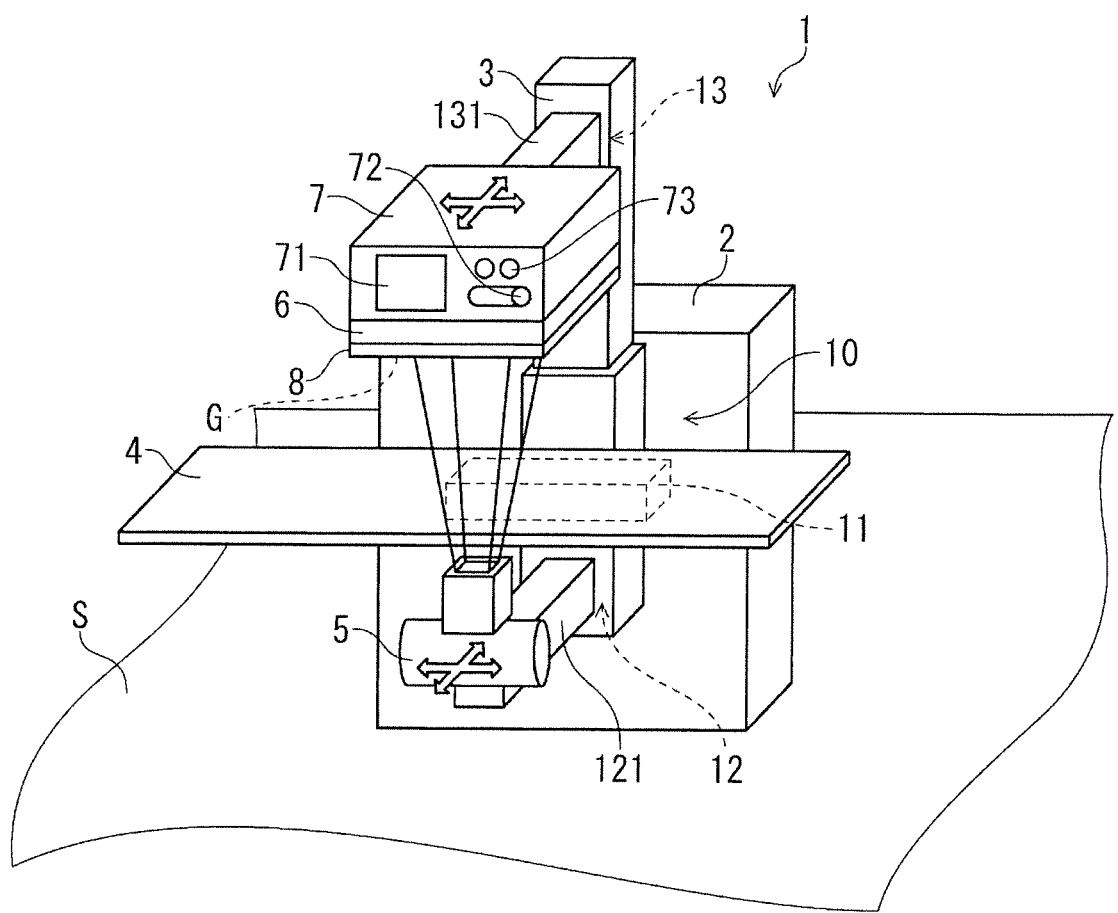
FIG. 7 is a schematic view illustrating the X-ray image diagnostic apparatus under an operation following the second action illustrated in FIG. 6A-6E.

FIG. 1 is a schematic diagram illustrating the overall configuration of an X-ray image diagnostic apparatus according to an embodiment of the present invention, FIG. 2 is a block diagram of the X-ray image diagnostic apparatus shown in FIG. 1, FIG. 3 is a diagram illustrating the positional relationship between an X-ray tube and a detector, FIGS. 4A and 4B are diagrams illustrating the relationship between a grid and a SID, FIGS. 5A, 5B and 5C are diagrams illustrating the positional relationship between an X-ray tube and a table (the first action), FIG. 6A, 6B, 6C, 6D, 6E are diagrams illustrating the positional relationship between an X-ray tube and a table (the second action), FIG. 7 is a schematic view illustrating the X-ray image diagnostic apparatus under an operation following the second action illustrated in FIGS. 6A-6E, and FIG. 8 is a diagram illustrating the positional relationship between an X-ray tube and a detector relative to the subject.

In addition, with respect to the respective diagrams, a characteristic portion may be enlarged for convenience sake in order to make some features easily understandable, and the dimensional ratios of respective components may be different from the actual ratios. Materials, dimensions, and the like exemplified below are only examples, and the present invention is not limited thereto and can be appropriately changed within a range not changing the gist of the present invention.

An X-ray image diagnostic apparatus 1 referring to FIG. 1 is an apparatus that takes an X-ray image to image the inside of a subject by emitting X-rays from the outside of the subject, such as a human body.

The X-ray image diagnostic apparatus 1 has a support unit (leg unit) 2, a main frame unit that is provided so as to be displaceable (movable up and down and rotatable) with respect to the support unit 2 and holds a table 4 (not shown), a tower unit 3 provided so as to be movable (slidable) with respect to the main frame unit, an X-ray tube (X-ray source) 5 and a detector 6 that are provided so as to be movable with respect to the tower unit 3, and an operation unit 7 fixed to the detector 6.

Under the state shown in FIG. 1, the X-ray tube 5 is disposed below the table 4 (on the back-surface side), and the detector 6 is disposed above the table 4 (on the top-surface side) so as to face the X-ray tube 5. Specifically, the X-ray image diagnostic apparatus 1 is a so-called under-table tube proximity fluoroscopic apparatus. According to such an X-ray image diagnostic apparatus 1, the exposure due to scattered rays against a user (such as a medical doctor) can be suppressed, so that the safety becomes much higher.

The support unit 2 is installed on an installation surface S of an imaging room where the X-ray image diagnostic apparatus 1 is installed. The support unit 2 has a function supporting each unit of the X-ray image diagnostic apparatus 1.

A main frame unit that holds the table 4 is attached to the support unit 2. The table 4 has a top-surface and a back-surface, and a subject is placed on the top-surface while lying down.

The tower unit 3 is attached to the main frame unit. The X-ray tube 5 and the detector 6 are respectively attached to the lower end portion and the upper end portion of the tower unit 3.

The X-ray tube 5 is connected with a high-power generation unit (not shown in FIG.) and generates X-rays, which are emitted to the subject, when a high voltage is added. On the other hand, the detector 6 includes an X-ray conversion unit (a plurality of semiconductor X-ray detection elements arranged in a matrix) thereinside and detects X-rays that are emitted from the X-ray tube 5 and penetrates the subject placed on the table 4.

The operation unit 7 is fixed to an upper portion of the detector 6. The operation unit 7 is a unit used when the user (such as a medical doctor) performs an operation to move the detector 6, and includes such as a monitor 71, an operation handle 72 and a switch 73.

In addition, as shown in FIG. 3, a mounting unit 8 capable of mounting the scattered ray removal grid G to the detector 6 and a grid detection unit 9 capable of detecting the presence or absence of mounting of the grid G onto the mounting unit 8 and the kind thereof are provided below the detector 6.

The mounting unit 8 includes, for example, a pair of rails for guiding the grid G by inserting two opposite edge portions (sides) of the grid G. therebetween.

The grid G has a characteristic (convergence) that allows only X-rays from the X-ray tube 5, for which the distance from the detector 6 (SID) is set to provide a predetermined value, to pass therethrough and does not allow scattered rays due to the subject to pass therethrough. Plural kinds of the grid G providing different convergence distances are available.

The kind of the grid G (i.e., the convergence distance) is detected by the grid detection unit 9. For example, the grid detection unit 9 can be formed from a photosensor that reads an optical pattern indicating the kind of the grid G or a magnetic sensor that reads magnetic data indicating the kind of the grid G. The optical pattern and the magnetic data are provided at the end portion of the grid G.

In addition, the X-ray image diagnostic apparatus 1 has a displacement mechanism 10 for supporting the main frame unit, which holds the table 4, so as to be movable up and down and rotatable with respect to the support unit 2, a tower unit moving mechanism 11 for supporting the tower unit 3 so as to be slidable with respect to the main frame unit, and an X-ray tube moving mechanism (first moving mechanism) 12 and a detector moving mechanism (second moving mechanism) 13 for supporting the X-ray tube 5 and the detector 6 so as to be movable with respect to the tower unit 3, respectively.

The displacement mechanism 10 moves (moves up and down) the table 4 (main frame unit) while horizontal (i.e., under the horizontal condition) together with the X-ray tube 5 and the detector 6 in the vertical direction and rotates (performs rotation movement) such elements with respect to the support unit 2.

The tower unit moving mechanism 11 slides the tower unit 3 in the longitudinal direction of the main frame unit (table 4). As a result, the X-ray tube 5 and the detector 6 slide in the longitudinal direction with respect to the table 4. In addition, the tower moving mechanism 11 enable the tower unit 3 to slide the main frame unit (table 4) in the width direction. Accordingly, the X-ray tube 5 and the detector 6 slide in the width direction relative to the table 4.

The X-ray tube moving mechanism 12 includes an arm 121, to which the X-ray tube 5 is fixed, and a motor (not shown) for moving the arm 121 along the longitudinal direction of the tower unit 3. The X-ray tube moving mechanism 12 is the moving mechanism to move the X-ray tube 5 in the direction approaching the table 4 or moving away therefrom (the direction perpendicular to the table 4) by rotating the motor to move the arm 121.

The detector moving mechanism 13 includes an arm 131 to which the detector 6 is fixed and a motor (not shown) for moving the arm 131 along the longitudinal direction of the tower unit 3. The detector moving mechanism 13 moves the detector 6 in the direction approaching or moving away from the table 4 (a direction perpendicular to the table 4) by rotating the motor to move the arm 131.

In addition, the detector 6 is structured to be movable (slidable) along the longitudinal direction of the arm 131. Therefore, when the detector 6 is retracted to the back position in the support unit 2 side, the detector 6 is not obstructive during an action in which the subject gets on and off of the table 4.

According to the configuration described above, the X-ray tube 5, the X-ray tube moving mechanism 12, the detector 6 and the detector moving mechanism 13 are installed to the tower unit 3; the tower unit 3 and the tower unit moving mechanism 11 are installed to the main frame unit; and main frame unit holds the table 4; so that the displacement mechanism 10 can collectively move (moved up and down) all elements relative to the support unit 2 in the vertical direction and collectively rotate all elements relative to the support unit 2.

The X-ray image diagnostic apparatus 1 comprises a control unit 14 connected with the X-ray tube 5, the detector 6, the operation unit 7, the grid detection unit 9, the displacement mechanism 10, the tower unit moving mechanism 11, the X-ray tube moving mechanism 12, and the detector moving mechanism 13.

The control unit 14 is a computer including such as a central processing unit (CPU), a read only memory (ROM), a random-access memory (RAM). The CPU executes a predetermined control program to control the action of the X-ray tube moving mechanism 12 and the detector moving mechanism 13, so that the control unit 14 can control the operation of each unit of the X-ray image diagnostic apparatus 1 in addition to the distance between the X-ray tube 5 and the detector 6.

Although the control unit 14 may individually control the movement of the X-ray tube 5 by the X-ray tube moving mechanism 12 and the movement of the detector 6 by the detector moving mechanism 13 without the movements being controlled in conjunction with each other, the operation of the X-ray tube moving mechanism 12 according to the embodiment of the present invention is controlled so that the X-ray tube 5 is moved interlockingly with the movement of the detector 6 by the detector moving mechanism 13.

Therefore, the movement of the detector 6 and the movement of the X-ray tube 5 interlockingly therewith can be performed under the control of the control unit 14 by just simply operating the operation unit 7. Therefore, the operability of the X-ray image diagnostic apparatus 1 is quite high, so that an X-ray imaging of the subject in accordance with the purpose can be performed as long as the positional relationship between the X-ray tube 5 and the detector 6 is set in advance.

In addition, the X-ray image diagnostic apparatus 1 comprises an image processing unit 15, a display unit 16, an input unit 17, and a (memory) storage unit 18 that are respectively connected to the control unit 14.

The image processing unit 15 is, for example, a computer including such as a CPU or a graphics processing unit (GPU). The image processing unit 15 executes a predetermined image processing program. The image processing unit 15 can be configured integrally with the control unit 14 by executing the image processing program using the same hardware (CPU) as for the control unit 14.

The display unit 16 can be, for example, made of such as a liquid crystal display and an organic EL display. The image generated by the image processing unit 15 is displayed on the display unit 16 under the control of the control unit 14.

The input unit 17 can be, for example, made of such as a keyboard and a mouse, a touch panel, and/or other controllers. The user (such as a medical doctor) performs various input operations through the input unit 17, and the control unit 14 receives such input operations.

The (memory) storage unit 18 can be a storage device such as a hard disk drive, for example. The storage unit 18 stores a control program and an image processing program, and in addition, stores the image data, imaging conditions, and a variety of setting values. Examples of the setting values include a value of SID corresponding to the kind of the grid G (convergence distance), ratios of the distance between the centerline in the thickness direction of the subject and each of the X-ray tube 5 or the detector 6, and so forth. In addition, the convergence distance of the grid G and the SID need not completely be the same and, for example, when the convergence distance of the grid G is 100 cm, the SID is set in the range of 80 cm to 120 cm.

Next, the inventors set forth the operation (usage) of the X-ray image diagnostic apparatus 1 when the SID is being kept constant.

First, a user (such as a medical doctor who is the operator) mounts the grid G to the mounting unit 8. The grid detection unit 9 detects that the grid G has been mounted on the mounting unit 8 and identifies (discriminates) the kind of the grid G. The identification (detection) signal is transmitted to the control unit 14, and then the control unit 14 determines the SID corresponding to the kind of the grid G based on the setting value stored in the storage unit 18.

Then, the user operates the operation handle 72 of the operation unit 7 vertically and horizontally so that the table 4 and the detector 6 are in a desired relative position. Through the above operation, the control unit 14 controls the action of the detector moving mechanism 13 so that the detector 6 moves in a direction approaching the table 4 or moving away therefrom and the action of the tower unit moving mechanism 11 so that the tower unit 3 slides in the longitudinal direction of the table 4 (main frame unit). Thereafter, the user presses the predetermined switch 73 of the operation unit 7 to start the emission of X-rays from the X-ray tube 5 to a region of interest of the subject (region to be imaged for diagnosis).

The X-rays emitted from the X-ray tube 5 penetrate the subject placed on the table 4 and are detected by the detector 6. The signal detected by the detector 6 is transmitted to the image processing unit 15, and an image (X-ray image) is generated. Such an image is displayed on the display unit 16 through the control unit 14.

Thereafter, the user operates the operation handle 72 of the operation unit 7 vertically and horizontally again to control (adjust) the relative position between the table 4 and the detector 6 in order to acquire an image of a different region of interest of the subject. At this time, the control unit 14 controls the action of the detector moving mechanism 13 in response to the user's operation using the operation unit 7 (i.e., the operator's input), and controls the action of the X-ray tube moving mechanism 12 so that the X-ray tube 5 moves interlockingly with the movement of the detector 6 by the detector moving mechanism 13. Specifically, the control unit 14 controls the action of the X-ray tube moving mechanism 12 so that the SID between the X-ray tube 5 and the detector 6 is being kept constant in the movable range of the X-ray tube 5.

According to the present embodiment, the control unit 14 controls the action of the X-ray tube moving mechanism 12 so that the SID (i.e., the constant SID) determined according to the kind of the grid G mounted on the mounting unit 8 is maintained. Here, as shown in FIGS. 4A, 4B, the grid G includes a transmission portion G1 that X-rays transmit and an absorption portion G2 that absorbs X-rays, and the transmission portion G1 and the absorption portion G2 are arranged so as to incline at a predetermined angle in the thickness direction of the grid G. According to the above configuration, when the convergence distance of the grid G and the SID could not match with each other due to the change of the SID, some of the X-rays emitted from the X-ray tube 5 are absorbed by the absorption portion G2 (in particular, the outer absorption portion G2), so that a uniform (even) X-ray image of the subject, as shown in FIG. 4B cannot be obtained.

In contrast, according to the present embodiment, the SID determined according to the kind of the grid G is being maintained, so that the convergence distance of the grid G and the SID always match with each other. Therefore, as shown in FIG. 4A, most of the X-rays emitted from the X-ray tube 5 pass through the transmission portion G1, so that a uniform X-ray image of the subject can be provided. As a result, an accurate diagnosis based on the obtained image can be performed.

In addition, the SID is being kept constant, so that it is not necessary to replace the grid G with another grid having a different convergence distance and as a result, the burden on the user does not increase.

Next, when the X-ray imaging of the subject ends, the user presses the predetermined switch 73 of the operation unit 7 to suspend the emission of X-rays from the X-ray tube 5 to the subject. At this time, when the table 4 (main frame unit) is not horizontal, the control unit 14 activates the displacement mechanism 10 to rotate the main frame unit with respect to the support unit 2 so that the table 4 turns horizontal.

Along with the above-described rotation of the main frame unit, the tower unit 3 also rotates, so that the longitudinal direction of the tower unit 3 coincides with the vertical direction.

The control unit 14 activates the X-ray tube moving mechanism 12 to move (lower) the X-ray tube 5 to the lowermost portion of the tower unit 3. At this time, the table 4 and the X-ray tube 5 are away from each other by a distance U1 as shown in FIG. 5A.

Thereafter, it is necessary to move (lower) the table 4 vertically downward as low as possible in order to make it easier for the subject to get off of the table 4. Therefore, in a case where the user presses the predetermined switch 73 of the operation unit 7, the control unit 14 activates the displacement mechanism 10 to move (lower) the horizontal table 4 (main frame unit) downward in the vertical direction together with the X-ray tube 5. At this time, as shown in FIG. 5B, the X-ray tube 5 approaches first of all the installation surface S on which the X-ray image diagnostic apparatus 1 is placed.

According to the present embodiment, the control unit 14 controls the action of the X-ray tube moving mechanism 12 so that the X-ray tube 5 moves in conjunction with the vertical movement of the horizontal table 4 by the displacement mechanism (lifting mechanism) 10. Specifically, when a distance T between the installation surface S and the X-ray tube 5 reaches a predetermined value as shown in FIG. 5B, the control unit 14 controls the action of the X-ray tube moving mechanism (moving mechanism) 12 so that the X-ray tube 5 moves (up) in a direction approaching the table 4 (upward vertically) as shown in FIG. 5C. The predetermined value of the distance T is not particularly limited, and preferably 10 cm or less, more preferably about in the range of 3 cm to 7 cm.

According to such a configuration (first operation) described above, the X-ray tube 5 can be prevented from colliding with the installation surface (floor surface) S to be damaged.

In addition, since an obstacle colliding with the installation surface S prior to the tower unit 3 disappears by moving the X-ray tube 5 upward vertically, the main frame unit that moves integrally with the tower unit 3 further can move downward in the vertical direction. Therefore, the table 4 held in the main frame unit can be brought closer to the installation surface S. As a result, the subject can easily get off of the table 4. At this time, the table 4 and the X-ray tube 5 move away from each other by a distance U2, which is shorter than the distance U1, as shown in FIG. 5C. In addition, needless to say, such an operation can be performed when the subject is placed on the table 4.

In addition, the X-ray image diagnostic apparatus 1 is structured to accomplish the second action (operation) additionally as set forth below. Referring to FIG. 6, FIG. 7, the inventors set forth such a second operation followed by the operation relative to the X-ray image diagnostic apparatus 1. Here, the inventors set forth mainly the different feature from the first operation and partially skip the explanation as to the same terms.

The user carries out suspending X-ray emission after the X-ray imaging of the subject ends. At this time, when the table 4 (main frame unit) is not horizontal, the control unit 14 activates the displacement mechanism 10 to turns the table 4 into the horizontal state.

Then the control unit 14 activates the X-ray tube moving mechanism 12 to move (lower) the X a-ray tube 5 to the lowermost position of the tower unit 3. At this time, the table 4 and the X-ray tube 5 are away from each other by a distance U1 as shown in FIG. 6A.

Then, the user presses the predetermined button 73 of the operation unit 7. According to such an operation, the control unit 14 activates the displacement mechanism 10 to lower the horizontal table 4 downward in the vertical direction together with the X-ray tube 5. At this time, as shown in FIG. 6B, the X-ray tube 5 approaches first of all the installation surface S. In addition, the table 4 and the X-ray tube 5 are lowered until the distance T between the installation surface S and the X-ray tube 5 reaches the predetermined value. Then, as shown in FIG. 6C, when the distance T reaches the predetermined value, the control unit 14 suspends once the table 4 and the X-ray tube 5 to down.

Referring to FIG. 6C, the table 4 is lowered to be enough height, so that the subject may not safely get off thereof with ease, in case. In such a case, the user should press the predetermined button 73 of the operation unit 7 further. According to such an operation, the unit 14 controls the action of the X-ray tube moving mechanism 12 so that the X-ray tube 5 moves up interlockingly with the table 4 being lowered by the displacement mechanism 10. Therefore, referring to FIG. 6D, whereas the table 4 as-is continues to move down, the X-ray tube 5 turns to move upward. Accordingly, the control unit 14 controls actions of the X-ray tube moving mechanism 12 and the displacement mechanism 10 while the table 4 is horizontal, so that the X-ray tube 5 moves upward in accordance with lowering the table 4.

In addition, the lifting level (amount) of the X-ray tube 5 is not particularly limited, for example, the level can be set as calculated based on the lowering level of the table 4. In such a case, it is preferable that a relational expression, (lifting level of X-ray tube 5)=k×(lowering level of the table 4), exists (wherein, k is an arbitrary positive number).

In addition, the timing when the X-ray tube 5 lifts is not limited to the timing when the distance T reaches the predetermined value can be as an arbitrarily timing.

In addition, referring to FIG. 6D, the speaker 19 embedded in the X-ray image diagnostic apparatus 1 sounds such as an alarm. According to such a feature, the user can be warned, for example, that a leg should not being caught in between the table 4 and the installation surface when the table 4 is further lowering. In addition, such a warning way is not limited to sounding, for example, turning on a light (lighting) and a combination of sound and lighting and so forth can be applied.

In addition, according to the X-ray image diagnostic apparatus 1, when the state is referred to FIG. 6D, i.e., the X-ray tube 5 turns from lowering to lifting, it is controlled that the emission of X-ray is forcibly suspended. Therefore, even if the user forgets the operation to suspend the X-ray emission after the X-ray imaging of the subject ends, it is absolutely preventable that the X-ray tube 5 gets closer to the subject on the table 4 resulting in excess X-ray exposure to the subject.

In addition, lowering of the table 4 and lifting of the X-ray tube 5 are continuously carried out until the table 4 and the X-ray tube 5 could be away from each other in the distance U2 which is shorter than the distance U1 and then suspend as shown in FIG. 6E. In addition, a sound from the speaker 19 also stops in association with such a suspension.

As set forth above, the second operation is also capable of preventing the collision between the X-ray tube 5 and the installation surface S, which causes any damage. In addition, when the second operation is completed. i.e., the state is referred to FIG. 6E, the table 4 is lowered to reach enough height, facilitating the subject to get off safely thereof with ease.

In addition, as described above, according to the X-ray image diagnostic apparatus 1, lowering of the X-ray tube 5 suspends once during second operation. Therefore, the user can make sure the operations of the X-ray tube 5, which is behind the table 4 and hard to see, from beginning of lowering to suspension and then after from the suspension to lifting of the X-ray tube 5, step-by-step. Accordingly, the safety while the X-ray image diagnostic apparatus 1 is being used is boosted for the user's sake and in addition, burden to pay much attention as to the X-ray tube 5 can be reduced.

In addition, the X-ray tube 5 is absolutely away from the installation surface S under the state referred to FIG. 6E, so that the user can smoothly slide the X-ray tube 5 and the detector 6 integrally in the longitudinal direction (direction from right to left indicated by the arrow in FIG. 7) and the width direction (orthogonal direction indicated by the arrow in FIG. 7) relative to the table 4 by operating the operation handle 72. Accordingly, the detector 6 together with the operation unit 7 can be retracted from the above of the subject, so that the space needed when the subject get up from and off of the table 4 can be ensured (reserved). In addition, such a space can be further expanded by retracting the detector 6 together with the operation unit 7 to the backside position of the supper unit 2 side the X-ray tube 5 independently from the X-ray tube 5.

In addition, according to the X-ray image diagnostic apparatus 1, the integrated sliding operation is carried out following the second operation referring to FIGS. 6A-6E, but the order of the second operation and the integrated sliding operation is not limited thereto, and for example, the integrated sliding operation can be followed by the second operation.

Here, in general, the inventors consider the case when the X-ray tube 5 cannot be lifted in association with lowering of the table 4. In such a case, the lowering limit (lowest position) of the table 4 is the point where the X-ray tube contacts with the installation surface S. And given the integrated sliding operation is carried out at the lowering limit, the X-ray tube 5 slides on the installation surface S resulting in causing such as damage and/or malfunction of the X-ray tube 5. Therefore, the integrated sliding operation must be carried out prior to letting lower the table 4 and the X-ray tube 5.

Whereas, as set forth above, the operation of the X-ray image diagnostic apparatus 1 can be carried out regardless the order of the second operation and the integrated sliding operation, so that the operation thereof is superior.

In addition, in some cases, the X-ray image diagnostic apparatus 1 may be used together with the X-ray tube (not shown in FIG.) hanging from the ceiling of the imaging room where the instant X-ray image diagnostic apparatus 1 is installed. In such a case, the hanging X-ray tube is used for imaging instead of the X-ray tube 5. And when the subject gets on the table 4, the second operation is first carried out to lower the table 4 enough and in addition, carry out the integrated sliding operation to ensure the space needed for the subject who is getting on the table 4 in the above of the table 4. According to such an operation, the subject can easily and safely get on the table 4, so that an expedited imaging is feasible.

According to the present embodiment, whereas the grid G is used in the case of taking an X-ray image of the subject, the grid G is not mandatory when using the X-ray image diagnostic apparatus 1. In such a case, the X-ray image diagnostic apparatus 1 is structured so that the user can set (determine) a constant SID by pressing the predetermined switch 73 of the operation unit 7 with the user's own discretion. For example, in the case of performing imaging using a contrast medium (barium), the user checks the contrast medium in the image displayed on the display unit 16 while operating the operation unit 7 to move the detector 6 vertically and horizontally. Then, when the user can clearly recognize the contrast medium in the image, the user can set the SID to a constant value by pressing the predetermined switch 73 of the operation unit 7. According to such a configuration described above, the movement of the contrast medium in the subject can be more accurately tracked.

In addition, when a relatively large SID is being kept constant, an image of the subject can be taken with X-rays that is almost like parallel lights. In such a case, an image with less distortion can be obtained.

Instead of keeping the distance (SID) between the X-ray tube 5 and the detector 6 constant, the control unit 14 can control the action of the X-ray tube moving mechanism 12 so that the enlargement ratio of the image of the subject by X-rays is being kept constant.

Also, in such a case, the control unit 14 controls the action of the X-ray tube moving mechanism 12 so that the X-ray tube 5 moves in the movable range of the X-ray tube 5.

Figure 8:
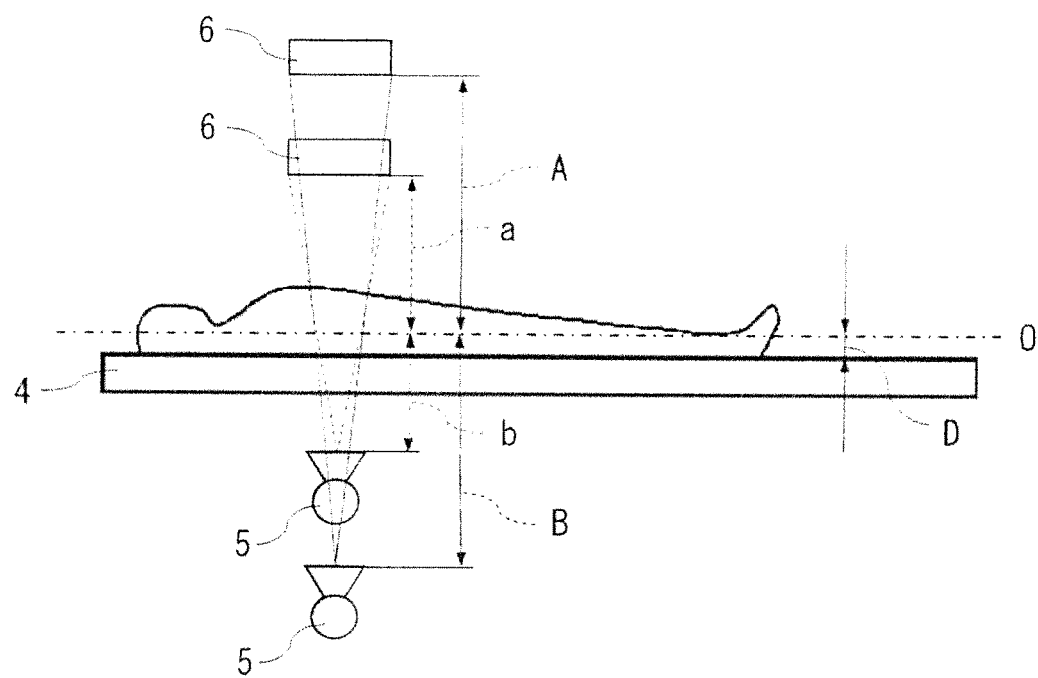
FIG. 8 is a diagram illustrating the positional relationship between an X-ray tube and a detector relative to the subject.

According to such a configuration described above, the control unit 14 keeps the ratio of the distance between the centerline O of the subject and the X-ray tube 5 and the distance between the centerline O of the subject and the detector 6 constant without taking the SID into consideration. Specifically, as shown in FIG. 8, the control unit 14 performs control such that a ratio of the distance a between the detector 6 and the centerline O and the distance b between the X-ray tube 5 and the centerline O is equal to a ratio of the distance A between the detector 6 and the centerline O and the distance B between the X-ray tube 5 and the centerline O.

For example, the user checks an observation (diagnosis) target in the image in the region of interest of the subject displayed on the display unit 16 while operating the operation unit 7 to move the detector 6 vertically and horizontally. Then, when the observation target in the image turns to a such size that can be easily recognized (visually recognized), the user can set the enlargement ratio of the image to a constant value by pressing the predetermined switch 73 of the operation unit 7. According to such a configuration described above, the size of image in different regions of interest of the subject displayed on the display unit 16 is not changed, so that it is easy to compare each size of observation (diagnosis) targets in the respective images. A distance D between the top-surface (front-surface) of the table 4 and the centerline O of the subject is set to, for example, about from 10 cm to 20 cm. Such a value may be input by the user through the input unit 17 prior to the start of use of the X-ray image diagnostic apparatus 1 or can be stored in advance in the storage unit 18. This value can be changed for each subject or fixed for all subjects.

The X-ray image diagnostic apparatus of the present invention has been set forth above, but the present invention is not limited to the configuration of the embodiment described above.

For example, the X-ray image diagnostic apparatus of the present invention can have any other arbitrary configuration added to the configuration of the embodiment described above or replaced with any configuration having the same function as the configuration of the embodiment described above. In addition, it should be considered that the embodiment disclosed herein is an example in all respects and is not restricted. The scope of the present invention is indicated not by the description of the above embodiment but by the scope of claims, and further includes meanings equivalent to the scope of claims and all changes (modification examples) within the scope. For example, the configuration (technology) for keeping the distance (SID) between the X-ray source and the detector or the enlargement ratio of the X-ray image of the subject constant can be applied to other X-ray image diagnostic apparatuses including an over-table tube proximity fluoroscopic table in which the positional relationship between the X-ray source and the detector with respect to the table is reversed.

In the embodiment described above, the main frame unit that holds the table 4 is supported so as to be movable up and down and rotatable with respect to the support unit 2, and the tower unit 3 is supported so as to be slidable with respect to the main frame unit. However, the present invention is not limited thereto. For example, the tower unit 3 can be supported so as to be movable up and down and rotatable with respect to the support unit 2, and the main frame unit that holds the table 4 can be supported so as to be slidable with respect to the tower unit 3.

REFERENCE OF SIGNS

1 X-ray image diagnosis apparatus
2 Support unit
3 Tower unit
4 Table
5 X-ray tube (X-ray source)
6 Detector
7 Operation unit
71 Monitor
72 Wheel (handle)
73 Switch
8 Mounting unit
9 Grid detection unit
10 Displaced mechanism
11 Tower unit moving mechanism
12 X-ray tube moving mechanism
121 Arm
13 Detector moving mechanism
131 Arm
14 Control unit
15 Image processing unit
16 Display
17 Input unit
18 (Memory) storage element
19 Speaker
G Grid
G1 Transmission portion
G2 Absorption portion
S Installation surface
T Distance
U1 Distance
U2 Distance
Centerline
a, A Distance between detector 6 and centerline O
b, B Distance between X-ray tube 5 and centerline O As used herein, a computing device includes some form of an input device for receiving data, an output device for outputting data in tangible form (e.g. printing or transmitting data, or displaying on a computer screen), a memory for storing data as well as computer code, and a processor/microprocessor for executing computer code wherein said computer code resident in the memory will physically cause said processor/microprocessor to read-in data via said input device, process said data within said microprocessor and output said processed data via said output device.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-ray image diagnostic apparatus and imaging devices, systems, and arrangements, including related radiotherapy operational controls and technologies of radiographic devices and all their sub components, including various circuits and components and combinations of circuits and combinations of components for such devices and for all related hand held type devices, without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, operating circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuit illustrations, step-modes, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or actions or algorithms described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

Those of skill in the particular art will be recognized as having and having access to sophisticated radiotherapy systems, circuits, and methods such that the skill level is high in science, technology, computers, programming, circuit design, and arrangement such that the described elements herein, after and following a review of this inventive disclosure and the inventive details herein, will be understood by those of skill in the art.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical of any kind developed now or later developed e.g. the computer hard drive, a removable disk or media such as a memory stick or SD media, or other electronic recording medium. The programs may also be run locally, on a station, or over an open or closed network without limitations thereto, for example, with a server or other machine sending signals to the local machine, which allows the local machine to carry out the operations described herein.

Also, the inventors intend that only those claims which use the words "means for" (specifically requiring the phrase "for" in "means for") are intended to be interpreted under 35 USC 112 (f) paragraph. Moreover, no limitations from the specification are intended to be read into any claims, unless those limitations are expressly included in the claims.

It will be further understood that the method steps described herein shall be understood additionally as descriptive algorithms for the operation of the enclosed units, switches, modes, and devices and units to which they apply.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray image diagnostic apparatus, comprising:
   a table that has a top-surface and a back-surface, wherein a subject is placed on said top-surface during a use of said X-ray image diagnostic apparatus;
   an X-ray source beneath said back-surface of said table and which emits X-rays to said subject;
   a detector that is disposed above said top-surface of said table to face said X-ray source and detect said X-rays emitted from said X-ray source and transmitted through said subject placed on said table;
   a first moving mechanism that moves said X-ray source in a direction approaching said table and a direction moving away from said table;
   a second moving mechanism that moves said detector in a direction approaching said table and a direction moving away from said table;
   a control unit that controls a distance between said X-ray source and said detector by controlling actions of said first moving mechanism and said second moving mechanism;
   wherein said control unit controls said action of said second moving mechanism in response to an input from an operator and further controls said action of said first moving mechanism that moves said X-ray source interlockingly with movement of said detector controlled thereby;
   wherein said control unit controls said action of said first moving mechanism that keeps said distance (SID i.e., source image distance) between said X-ray source and said detector being constant within a movable range of said X-ray source;
   said X-ray image diagnostic apparatus, further comprising:
   a mounting unit that mounts a scattered ray removal grid on said detector; and
   wherein said control unit determines said distance based on a kind of said grid.

2. The X-ray image diagnostic apparatus, according to claim 1, further comprising:
   a grid detection unit that detects a mounting of said grid on said mounting unit and the kind of said grid; and
   wherein said control unit determines said distance based on said kind of said grid detected by said grid detection unit.

3. The X-ray image diagnostic apparatus, according to claim 1, wherein:
   said control unit controls said action of said first moving mechanism so that an enlargement ratio of an image of said subject, obtained by using said X-rays, is being constant.

4. The X-ray image diagnostic apparatus, according to claim 1, further comprising:
   a lifting mechanism that moves up-and-down said first moving mechanism together with said second moving mechanism when said table is horizontal; and
   wherein said control unit controls said action of said first moving mechanism so that said X-ray source moves interlockingly with said table that moves up-and-down using said lifting mechanism when said table is horizontal.

5. The X-ray image diagnostic apparatus, according to claim 4, wherein:
   said control unit controls said action of said first moving mechanism so that said X-ray source moves in an approaching direction to said table when a distance between an installation surface on which said X-ray image diagnostic apparatus is placed and said X-ray source is a predetermined value.

6. An X-ray image diagnostic apparatus, comprising:
   a table that has a top-surface and a back-surface, wherein during a use a subject is placed on the top-surface of said table;
   an X-ray source that is disposed below said back-surface of the table and emits X-rays to said subject;
   a detector that is disposed above said top-surface of said table to face said X-ray source and which detects said X-rays emitted from said X-ray source and transmitted through said subject placed on said table;
   a moving mechanism that moves the X-ray source in a direction approaching said table and moving away therefrom;
   a lifting mechanism that lifts said table together with said moving mechanism when said table is horizontal; and
   a control unit that controls lifting said X-ray source in association with lowering said table by controlling actions of said moving mechanism and said lifting mechanism.

7. The X-ray image diagnostic apparatus, according to claim 6, wherein:
said control unit controls said action of said moving mechanism so that said X-ray source lifts when a distance between an installation surface and said X-ray source provides a predetermined value, and said X-ray image diagnostic apparatus is installed on said installation surface.

8. The X-ray image diagnostic apparatus, according to claim 6, wherein:
said control unit lowers said table and said X-ray source until a distance provides a predetermined value by controlling an action of said lifting mechanism; suspends once lowering said table and said X-ray source when said distance provides said predetermined value; and then lifts said X-ray source by controlling said action of said moving mechanism.

9. An X-ray image diagnostic apparatus, comprising:
a table that has a top-surface and a back-surface, wherein a subject is placed on said top-surface during a use of said X-ray image diagnostic apparatus;
an X-ray source beneath said back-surface of said table and which emits X-rays to said subject;
a detector that is disposed above said top-surface of said table to face said X-ray source and detect said X-rays emitted from said X-ray source and transmitted through said subject placed on said table;
a first moving mechanism that moves said X-ray source in a direction approaching said table and a direction moving away from said table;
a second moving mechanism that moves said detector in a direction approaching said table and a direction moving away from said table;
a control unit that controls a distance between said X-ray source and said detector by controlling actions of said first moving mechanism and said second moving mechanism;
a lifting mechanism that moves up-and-down said first moving mechanism together with said second moving mechanism when said table is horizontal; and
wherein said control unit controls said action of said first moving mechanism so that said X-ray source moves interlockingly with said table that moves up-and-down using said lifting mechanism when said table is horizontal.

10. The X-ray image diagnostic apparatus, according to claim 9, wherein:
said control unit controls said action of said first moving mechanism so that said X-ray source moves in an approaching direction to said table when a distance between an installation surface on which said X-ray image diagnostic apparatus is placed and said X-ray source is a predetermined value.

\* \* \* \* \*